US008398649B2

(12) United States Patent
Koulisis et al.

(10) Patent No.: US 8,398,649 B2
(45) Date of Patent: Mar. 19, 2013

(54) ARTICULATING TRANSFORAMINAL LUMBAR INTERBODY FUSION INSERTER DEVICE AND ASSOCIATED METHOD OF USE

(75) Inventors: Christo Koulisis, Niceville, FL (US); David Crook, Mineola, TX (US)

(73) Assignee: US Spine, Inc., Salt Lake City, UT (US)

( * ) Notice: Subject to any disclaimer, the term of this patent is extended or adjusted under 35 U.S.C. 154(b) by 924 days.

(21) Appl. No.: 12/187,064

(22) Filed: Aug. 6, 2008

(65) Prior Publication Data
US 2009/0043312 A1    Feb. 12, 2009

Related U.S. Application Data

(60) Provisional application No. 60/954,132, filed on Aug. 6, 2007.

(51) Int. Cl.
*A61B 17/56* (2006.01)
(52) U.S. Cl. .......................................................... 606/99
(58) Field of Classification Search ................ 606/86 A, 606/99
See application file for complete search history.

(56) References Cited

U.S. PATENT DOCUMENTS

| | | | |
|---|---|---|---|
| 7,470,273 B2 * | 12/2008 | Dougherty-Shah | 606/86 A |
| 7,901,458 B2 * | 3/2011 | DeRidder et al. | 623/17.11 |
| 7,976,549 B2 * | 7/2011 | Dye et al. | 606/99 |
| 7,988,695 B2 * | 8/2011 | Dye | 606/86 A |
| 2004/0153065 A1 * | 8/2004 | Lim | 606/53 |
| 2005/0096745 A1 * | 5/2005 | Andre et al. | 623/17.11 |
| 2006/0229627 A1 * | 10/2006 | Hunt et al. | 606/86 |
| 2006/0235426 A1 * | 10/2006 | Lim et al. | 606/99 |
| 2006/0241761 A1 * | 10/2006 | Gately | 623/17.11 |
| 2007/0225726 A1 * | 9/2007 | Dye et al. | 606/99 |
| 2007/0225808 A1 * | 9/2007 | Warnick | 623/17.11 |
| 2008/0009880 A1 * | 1/2008 | Warnick et al. | 606/99 |
| 2008/0077153 A1 * | 3/2008 | Pernsteiner et al. | 606/99 |

* cited by examiner

*Primary Examiner* — Nicholas Woodall
(74) *Attorney, Agent, or Firm* — Phillips Ryther & Winchester; Matthew D. Thayne

(57) ABSTRACT

The present invention provides an articulating TLIF inserter device operable for placing, positioning, and inserting a spinal implant into an intervertebral space with minimum tissue disruption and maximum inline impaction forces, including: an elongate shaft having a proximal end, a distal end, and an axis; an ergonomic handle disposed at the proximal end of the elongate shaft; an articulating joint mechanism disposed at the distal end of the elongate shaft; and an inserter piece coupled to the articulating joint mechanism, wherein the inserter piece is operable for selectively retaining the spinal implant, and wherein the articulating joint mechanism is operable for selectively actuating the inserter piece between one or more substantially off-axis configurations and a substantially on-axis configuration with respect to the elongate shaft. The articulating TLIF inserter device also includes a release mechanism disposed one of at and near the ergonomic handle, wherein the release mechanism is coupled to and operable for selectively actuating the articulating joint mechanism.

24 Claims, 5 Drawing Sheets

ARTICULATING TRANSFORAMINAL LUMBAR INTERBODY FUSION INSERTER DEVICE AND ASSOCIATED METHOD OF USE

CROSS-REFERENCE TO RELATED APPLICATION

The present non-provisional patent application claims the benefit of priority of U.S. Provisional Patent Application No. 60/954,132, filed on Aug. 6, 2007, and entitled "ARTICULATING TRANSFORAMINAL LUMBAR INTERBODY FUSION INSERTER DEVICE AND ASSOCIATED METHOD OF USE," the contents of which are incorporated in full by reference herein.

FIELD OF THE INVENTION

The present invention relates generally to devices and methods for performing spinal and other surgical procedures. More specifically, the present invention relates to an articulating transforaminal lumbar interbody fusion (TLIF) inserter device and an associated method of use. This TLIF inserter device is configured to relatively simply and easily place and position bone grafts and/or spinal implants in the intervertebral disc spaces of the spine of a patient. Advantageously, the TLIF inserter device is alternatively substantially curved to minimize tissue disruption and substantially straight to maximize inline impaction forces.

BACKGROUND OF THE INVENTION

For patients with varying degrees of spondylolisthesis, degenerative disc disease, and/or nerve compression with associated lower back pain, spinal fusion surgery, or lumbar arthrodesis, is an effective and commonly used treatment. Spinal fusion surgery involves distracting or decompressing one or more intervertebral spaces, removing the associated disc(s), and joining or fusing two or more adjacent vertebrae together using a bone graft and/or spinal implant. The five main types of lumbar arthrodesis include: posterior lumbar fusion (PLF), posterior lumbar interbody fusion (PLIF), anterior lumbar interbody fusion (ALIF), circumferential 360 fusion, and TLIF.

PLF, utilizing a back (posterior) approach, with pedicle screws, plates, or the like is relatively simple, safe, and allows for good posterior decompression. However, it does not remove the disc or immobilize the segment very effectively. PLIF, also utilizing a back (posterior) approach, with pedicle screws, plates, or the like removes the disc and immobilize the segment effectively, but nerve roots may be moved and damaged, and there is a risk of neural lesions. ALIF, utilizing a front (anterior) approach, with pedicle screws, plates, or the like also removes the disc and immobilize the segment effectively, but again nerve roots and blood vessels may be moved and damaged, and there is a risk of neural lesions. Circumferential 360 fusion, utilizing a back-and-front approach, combines the advantages and disadvantages of the posterior and anterior methods.

In recent years, many spinal surgeons have begun to use TLIF instead of PLIF or other methods. The main advantage of TLIF over PLIF and other methods is that it allows for complete removal of the disc through the vertebral foramen and decompression of the spinal canal and vertebral foramen with minimum risk of neural lesion, as access is lateral to the nerve roots.

Conventional TLIF inserter devices are fixed, static devices that are mutually exclusively either substantially curved (in order to minimize tissue disruption during initial spinal implant placement and subsequent positioning) or substantially straight (in order to maximize inline impaction forces during final spinal implant positioning). Thus, what is needed in the art is a TLIF inserter device that is flexible and dynamic, and that is alternatively substantially curved to minimize tissue disruption and substantially straight to maximize inline impaction forces.

BRIEF SUMMARY OF THE INVENTION

The present invention relates generally to devices and methods for performing spinal and other surgical procedures. More specifically, the present invention relates to an articulating TLIF inserter device and an associated method of use. This TLIF inserter device is configured to relatively simply and easily place and position bone grafts and/or spinal implants in the intervertebral disc spaces of the spine of a patient. Advantageously, the TLIF inserter device is alternatively substantially curved to minimize tissue disruption and substantially straight to maximize inline impaction forces.

In one exemplary embodiment, the present invention provides an articulating transforaminal lumbar interbody fusion inserter device operable for placing, positioning, and inserting a spinal implant into an intervertebral space with minimum tissue disruption and maximum inline impaction forces, including: an elongate shaft having a proximal end, a distal end, and an axis; an ergonomic handle disposed at the proximal end of the elongate shaft; an articulating joint mechanism disposed at the distal end of the elongate shaft; and an inserter piece coupled to the articulating joint mechanism, wherein the inserter piece is operable for selectively retaining the spinal implant, and wherein the articulating joint mechanism is operable for selectively actuating the inserter piece between one or more substantially off-axis configurations and a substantially on-axis configuration with respect to the elongate shaft. The articulating transforaminal lumbar interbody fusion inserter device also includes a release mechanism disposed one of at and near the ergonomic handle, wherein the release mechanism is coupled to and operable for selectively actuating the articulating joint mechanism. Optionally, the elongate shaft is substantially cylindrical and hollow. The release mechanism is coupled to and operable for selectively actuating the articulating joint mechanism via one or more of a rod and a wire disposed through the elongate shaft. The articulating joint mechanism includes a base, a slotted capstan pivotably coupled to the base, and a locking bar configured to selectively engage/disengage the slotted capstan. The inserter piece includes one or more of a retention tool and a cutting tool. Optionally, the articulating joint mechanism is operable for selectively actuating the inserter piece between one or more substantially 30 to 40-degree off-axis configurations and a substantially 0-degree on-axis configuration with respect to the elongate shaft. Optionally, the inserter piece is selectively articulatable with respect to the articulating joint mechanism.

In another exemplary embodiment, the present invention provides an articulating surgical device operable for placing, positioning, and inserting a surgical implant into or otherwise manipulating an anatomical space with minimum tissue disruption and maximum inline impaction forces, including: an elongate shaft having a proximal end, a distal end, and an axis; an ergonomic handle disposed at the proximal end of the elongate shaft; an articulating joint mechanism disposed at the distal end of the elongate shaft; and a surgical tool coupled to the articulating joint mechanism, wherein the surgical tool is operable for one of selectively retaining the surgical implant and manipulating the anatomical space, and wherein the articulating joint mechanism is operable for selectively actuating the surgical tool between one or more substantially off-axis configurations and a substantially on-axis configuration with respect to the elongate shaft. The articulating surgical device also includes a release mechanism disposed one of at and near the ergonomic handle, wherein the release mechanism is coupled to and operable for selectively actuating the articulating joint mechanism. Optionally, the elongate shaft is substantially cylindrical and hollow. The release mechanism is coupled to and operable for selectively actuating the articulating joint mechanism via one or more of a rod and a wire disposed through the elongate shaft. The articulating joint mechanism includes a base, a slotted capstan pivotably coupled to the base, and a locking bar configured to selectively engage/disengage the slotted capstan. The surgical tool includes one or more of a retention tool and a cutting tool. Optionally, the articulating joint mechanism is operable for selectively actuating the surgical tool between one or more substantially 30 to 40-degree off-axis configurations and a substantially 0-degree on-axis configuration with respect to the elongate shaft. Optionally, the surgical tool is selectively articulatable with respect to the articulating joint mechanism.

In a further exemplary embodiment, the present invention provides a transforaminal lumbar interbody fusion method for placing, positioning, and inserting a spinal implant into an intervertebral space with minimum tissue disruption and maximum inline impaction forces, including: providing an elongate shaft having a proximal end, a distal end, and an axis; providing an ergonomic handle disposed at the proximal end of the elongate shaft; providing an articulating joint mechanism disposed at the distal end of the elongate shaft; and providing an inserter piece coupled to the articulating joint mechanism, wherein the inserter piece is operable for selectively retaining the spinal implant, and wherein the articulating joint mechanism is operable for selectively actuating the inserter piece between one or more substantially off-axis configurations and a substantially on-axis configuration with respect to the elongate shaft. The transforaminal lumbar interbody fusion method also includes providing a release mechanism disposed one of at and near the ergonomic handle, wherein the release mechanism is coupled to and operable for selectively actuating the articulating joint mechanism. Optionally, the elongate shaft is substantially cylindrical and hollow. The release mechanism is coupled to and operable for selectively actuating the articulating joint mechanism via one or more of a rod and a wire disposed through the elongate shaft. The articulating joint mechanism includes a base, a slotted capstan pivotably coupled to the base, and a locking bar configured to selectively engage/disengage the slotted capstan. The inserter piece includes one or more of a retention tool and a cutting tool. Optionally, the articulating joint mechanism is operable for selectively actuating the inserter piece between one or more substantially 30 to 40-degree off-axis configurations and a substantially 0-degree on-axis configuration with respect to the elongate shaft. Optionally, the inserter piece is selectively articulatable with respect to the articulating joint mechanism.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Again, the present invention relates generally to devices and methods for performing spinal and other surgical procedures. More specifically, the present invention relates to an articulating TLIF inserter device and an associated method of use. This TLIF inserter device is configured to relatively simply and easily place and position bone grafts and/or spinal implants in the intervertebral disc spaces of the spine of a patient. Advantageously, the TLIF inserter device is alternatively substantially curved to minimize tissue disruption and substantially straight to maximize inline impaction forces.

Figure 1:
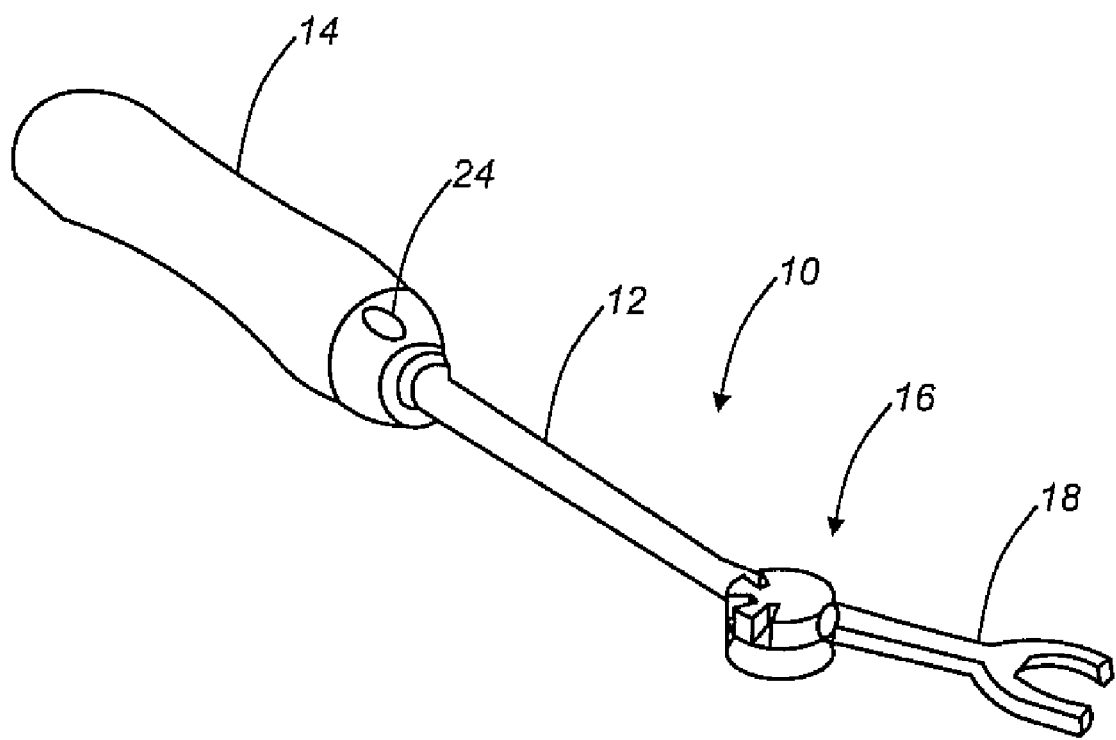
FIG. 1 is a perspective view illustrating one exemplary embodiment of the TLIF inserter device of the present invention, the shaft and inserter piece of the TLIF inserter device in an off-axis initial placement and positioning configuration.
Figure 2:
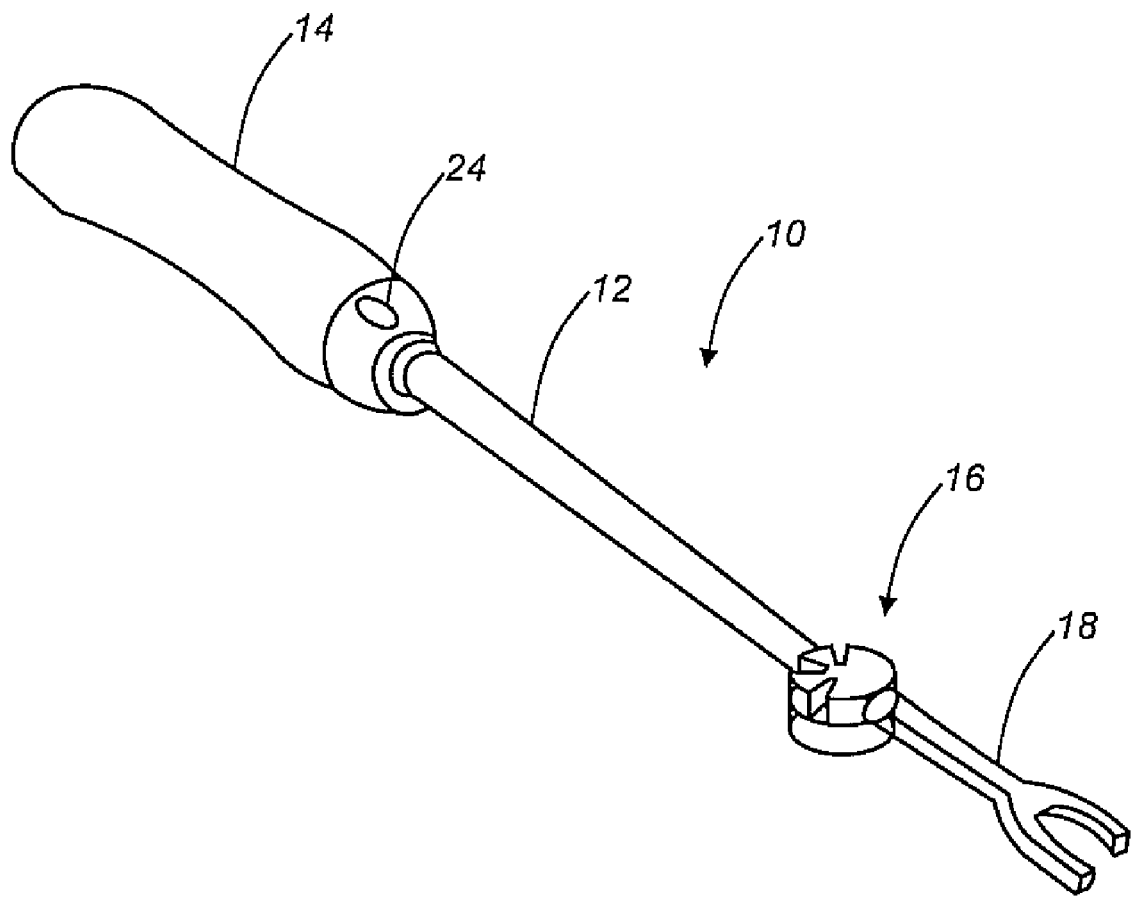
FIG. 2 is another perspective view illustrating the TLIF inserter device of FIG. 1, the shaft and inserter piece of the TLIF inserter device in an on-axis final impaction and positioning configuration.

Referring to FIGS. 1 and 2, in one exemplary embodiment, the TLIF inserter device 10 of the present invention includes an elongate shaft 12 having an ergonomic handle 14 on its proximal end and an articulating joint mechanism 16 on its distal end. An inserter piece 18 or the like rides on the articulating joint mechanism 16, and is selectively movable from off-axis with the shaft 12 (FIG. 1) and on-axis with the shaft 12 (FIG. 2). In one exemplary embodiment, the shaft 12 is substantially cylindrical and hollow. The articulating joint mechanism 16 is coupled to and selectively actuated by a release mechanism 24 that is disposed on or adjacent to the handle. More specifically, the articulating joint mechanism 16 is coupled to and selectively actuated by the release mechanism 24 via one or more rods, wires, or the like disposed through the shaft 12. The release mechanism 24 may actuate the articulating joint mechanism 16 via finger rotation-and-release, finger push-and-release, etc. Advantageously, the TLIF inserter device 10 is alternatively substantially curved when in an off-axis initial placement and positioning configuration (FIG. 1) to minimize tissue disruption and substantially straight when in an on-axis final impaction and positioning configuration (FIG. 2) to maximize inline impaction forces. The force exerted through the TLIF inserter device 10 is used to efficiently advance a spinal implant into an intervertebral disc space, by hand and/or with the assistance of an impaction tool. The inserter piece 18 retains the spinal implant at all relevant times. Optionally, the inserter piece 18 is replaced with a threaded connector or the like that is configured to engage the spinal implant, a cutting tool, etc.

Figure 3:
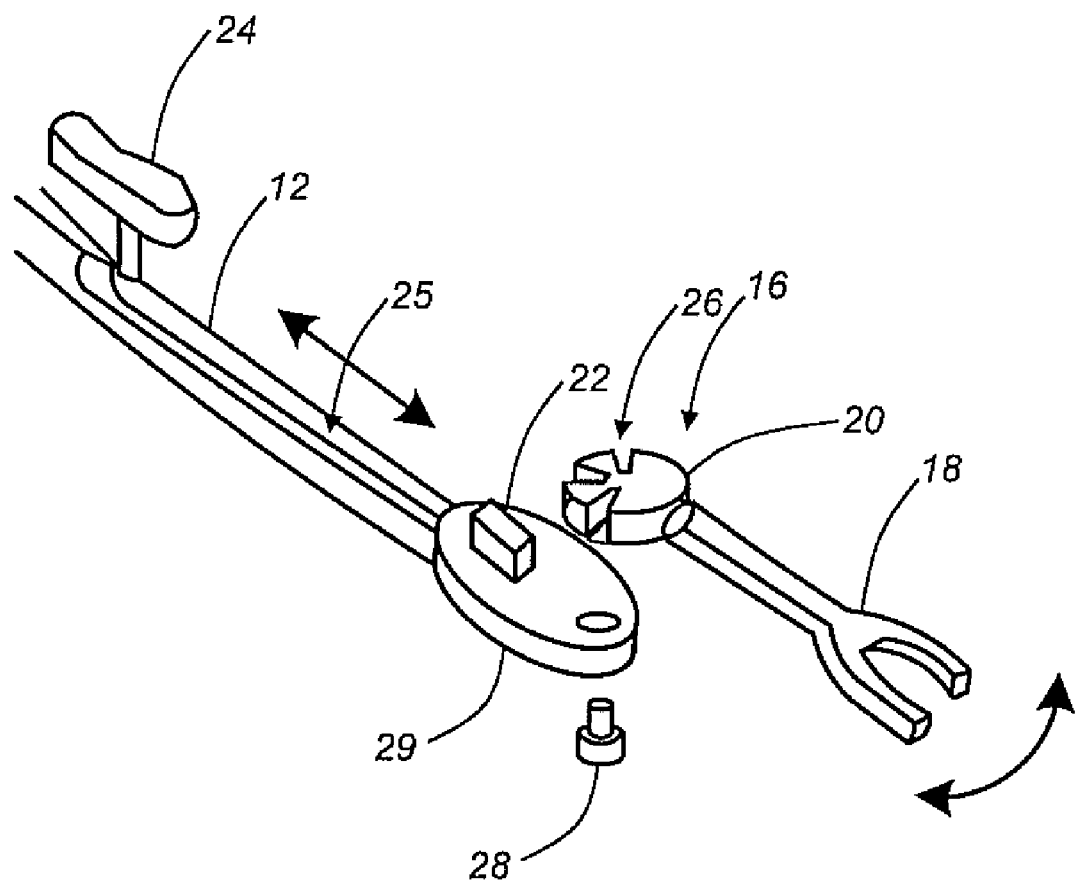
FIG. 3 is an exploded perspective view illustrating one exemplary embodiment of the articulating joint mechanism (i.e. slotted capstan and associated locking bar) and associated release mechanism of the TLIF inserter device of FIGS. 1 and 2.
Figure 4:
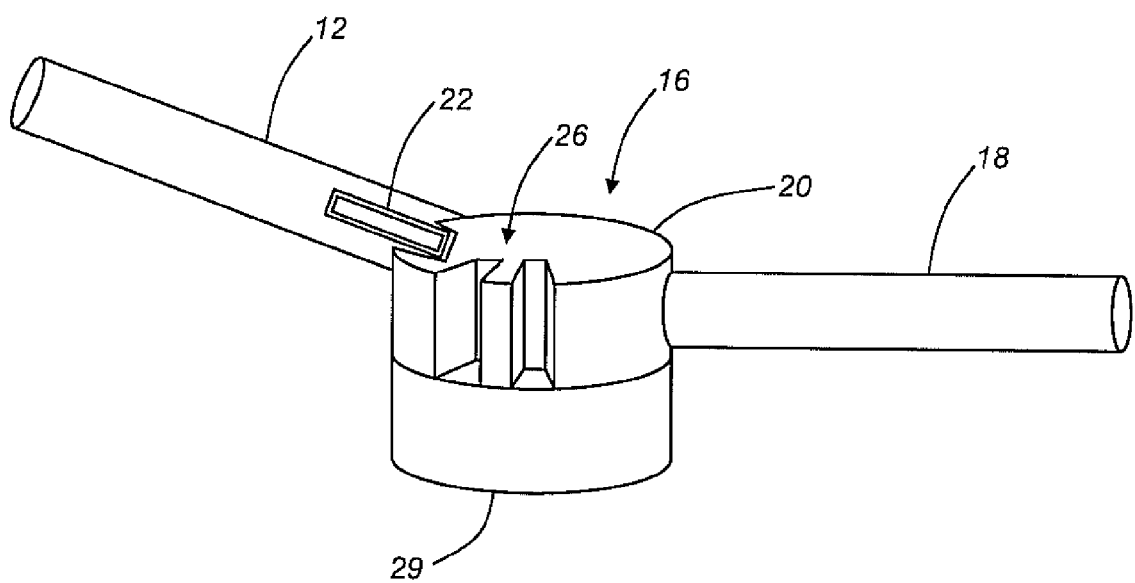
FIG. 4 is a partial perspective view illustrating the articulating joint mechanism (i.e. slotted capstan and associated locking bar) of FIG. 3 in the off-axis initial placement and positioning configuration.
Figure 5:
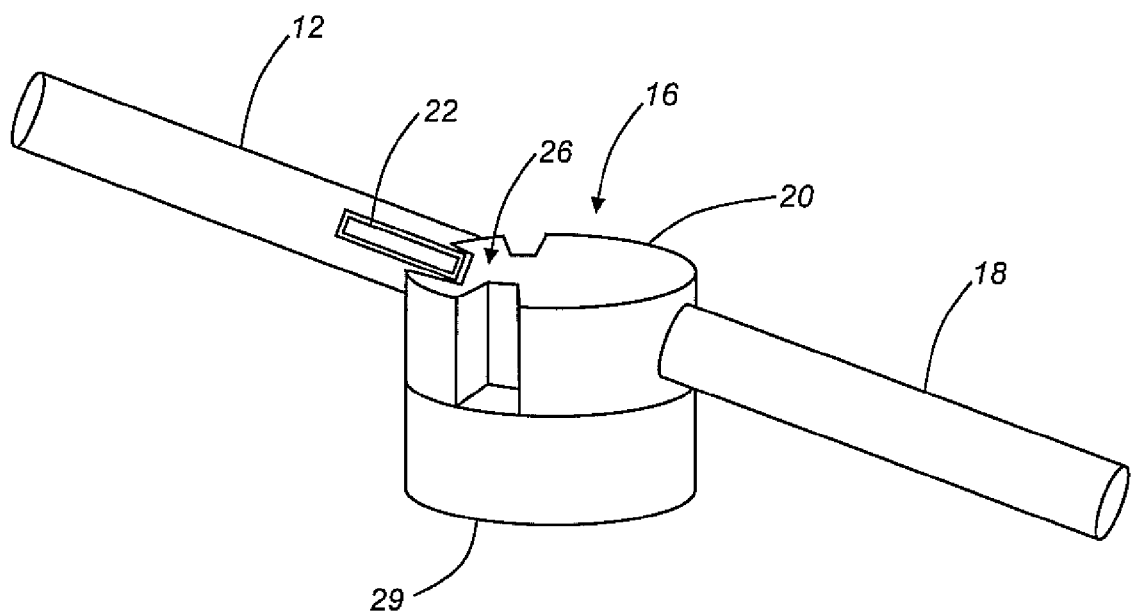
FIG. 5 is another partial perspective view illustrating the articulating joint mechanism (i.e. slotted capstan and associated locking bar) of FIG. 3 in the on-axis final impaction and positioning configuration.

Referring to FIG. 3, in one exemplary embodiment, the articulating joint mechanism 16 consists of a slotted capstan 20 or the like and corresponding locking bar 22 or the like that are actuated via the release mechanism 24 on or near the handle 14 (FIG. 1) through the one or more rods, wires, or the like 25 disposed through the shaft 12. Specifically, the release mechanism 24 is actuated, causing the locking bar 22 to move either proximally or distally along the shaft 12, thereby disengaging or engaging one of a plurality of slots 26 associated with the slotted capstan 20. When the locking bar 22 is disengaged from a given slot 26, the slotted capstan 20 may be pivoted about a retaining pin 28 disposed through a base 29 and advanced to another slot 26 prior to engagement. Thus, various angles may be selected for the inserter piece 18 relative to the shaft 12. It should be noted that, in the illustrated embodiment, three slots 26 are provided, corresponding to three inserter piece angles (+/−30-40 degrees off-axis (see FIG. 4) and 0 degrees off-axis (see FIG. 5)), however, more or fewer slots 26 may be provided. Other articulating joint mechanisms and release mechanisms may also be utilized.

It should be noted that the inserter piece 18 may also be equipped with an articulation feature, and may consist of other implements. These other implements could include threaded implements, cutting implements, etc., as described above.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the invention, are contemplated thereby, and are intended to be covered by the following claims.

What is claimed is:

1. An articulating transforaminal lumbar interbody fusion inserter device operable for placing, positioning, and inserting a spinal implant into an intervertebral space with minimum tissue disruption and maximum inline impaction forces, comprising:
    a first elongate shaft having a proximal end, a distal end, and an axis;
    a handle disposed at the proximal end of the first elongate shaft;
    an articulating joint mechanism disposed at the distal end of the first elongate shaft; and
    an inserter piece coupled to the articulating joint mechanism, wherein the inserter piece is operable for selectively retaining the spinal implant, and wherein the inserter piece comprises a second elongate shaft, and
    wherein the articulating joint mechanism is operable for selectively actuating the inserter piece between a plurality of substantially off-axis configurations and a substantially on-axis configuration with respect to the first elongate shaft such that the second elongate shaft extends substantially along the axis of the first elongate shaft in the on-axis configuration and such that the second elongate shaft extends at an angle relative to the first elongate shaft in the off-axis configuration, and wherein the articulating joint mechanism comprises a base, a slotted capstan pivotably coupled to the base, and a locking bar configured to selectively engage/disengage the slotted capstan.

2. The articulating transforaminal lumbar interbody fusion inserter device of claim 1, further comprising a release mechanism disposed one of at and near the handle, wherein the release mechanism is coupled to and operable for selectively actuating the articulating joint mechanism.

3. The articulating transforaminal lumbar interbody fusion inserter device of claim 2, wherein the first elongate shaft is substantially cylindrical and hollow.

4. The articulating transforaminal lumbar interbody fusion inserter device of claim 3, wherein the release mechanism is coupled to and operable for selectively actuating the articulating joint mechanism via one or more of a rod and a wire disposed through the first elongate shaft.

5. The articulating transforaminal lumbar interbody fusion inserter device of claim 1, wherein the inserter piece comprises one or more of a retention tool and a cutting tool.

6. The articulating transforaminal lumbar interbody fusion inserter device of claim 1, wherein the articulating joint mechanism is operable for selectively actuating the inserter piece between one or more substantially 30 to 40-degree off-axis configurations and a substantially 0-degree on-axis configuration with respect to the first elongate shaft.

7. The articulating transforaminal lumbar interbody fusion inserter device of claim 1, wherein the inserter piece is selectively articulatable with respect to the articulating joint mechanism.

8. The articulating transforaminal lumbar interbody fusion inserter device of claim 1, wherein the articulating joint mechanism is operable for selectively actuating the inserter piece between one or more substantially 30 to 40-degree off-axis configurations and a substantially 0-degree on-axis configuration with respect to the first elongate shaft.

9. The articulating transforaminal lumbar interbody fusion inserter device of claim 1, wherein the articulating joint mechanism is operable for selectively actuating the inserter piece between a plurality of discrete substantially off-axis configurations and a substantially on-axis configuration with respect to the elongate shaft.

10. An articulating surgical device operable for placing, positioning, and inserting a surgical implant into or otherwise manipulating an anatomical space with minimum tissue disruption and maximum inline impaction forces, comprising:
    an elongate shaft having a proximal end, a distal end, and an axis;
    a handle disposed at the proximal end of the elongate shaft;
    an articulating joint mechanism disposed at the distal end of the elongate shaft; and
    a surgical tool coupled to the articulating joint mechanism at the distal end of the articulating joint mechanism,
    wherein the surgical tool is operable for one of selectively retaining the surgical implant and manipulating the anatomical space,
    wherein the articulating joint mechanism is operable for selectively actuating the surgical tool between a plurality of substantially off-axis configurations and a substantially on-axis configuration with respect to the elongate shaft, and
    wherein the articulating joint mechanism comprises a base, a slotted capstan pivotably coupled to the base, and a locking bar configured to selectively engage/disengage the slotted capstan.

11. The articulating surgical device of claim 10, further comprising a release mechanism disposed one of at and near the handle, wherein the release mechanism is couple to and operable for selectively actuating the articulating joint mechanism.

12. The articulating surgical device of claim 11, wherein the elongate shaft is substantially cylindrical and hollow.

13. The articulating surgical device of claim 12, wherein the release mechanism is coupled to and operable for selectively actuating the articulating joint mechanism via one or more of a rod and a wire disposed through the elongate shaft.

14. The articulating surgical device of claim 10, wherein the surgical tool comprises one or more of a retention tool and a cutting tool.

15. The articulating surgical device of claim 10, wherein the articulating joint mechanism is operable for selectively actuating the surgical tool between one or more substantially 30 to 40-degree off-axis configurations and a substantially 0-degree on-axis configuration with respect to the elongate shaft.

16. The articulating surgical device of claim 10, wherein the surgical tool is selectively articulatable with respect to the articulating joint mechanism.

17. The articulating surgical device of claim 10, wherein the articulating joint mechanism is operable for selectively actuating the surgical tool between a plurality of discrete substantially off-axis configurations and a substantially on-axis configuration with respect to the elongate shaft.

18. A transforaminal lumbar interbody fusion method for placing, positioning, and inserting a spinal implant into an intervertebral space with minimum tissue disruption and maximum inline impaction forces, comprising:
providing an articulating surgical device, the articulating surgical device comprising:
an elongate shaft
an articulating joint mechanism disposed at the distal end of the elongate shaft, wherein the articulating joint mechanism comprises a base, a slotted capstan pivotably coupled to the base, and a locking bar configured to selectively engage/disengage the slotted capstan; and
an inserter piece coupled to the articulating joint mechanism;
selectively retaining the spinal implant with the inserter piece;
inserting the spinal implant into an intervertebral disc space with the articulating surgical device; and
selectively actuating the inserter piece between a plurality of substantially off-axis configurations and a substantially on-axis configuration with respect to the elongate shaft such that the inserter piece pivots with respect to the articulating joint mechanism without the spinal implant pivoting with respect to the inserter piece.

19. The transforaminal lumbar interbody fusion method of claim 18, further comprising actuating a release mechanism, wherein the release mechanism actuates the articulating joint mechanism.

20. The transforaminal lumbar interbody fusion method of claim 19, wherein the elongate shaft is substantially cylindrical and hollow.

21. The transforaminal lumbar interbody fusion method of claim 20, wherein the release mechanism actuates the articulating joint mechanism via one or more of a rod and a wire disposed through the elongate shaft.

22. The transforaminal lumbar interbody fusion method of claim 18, wherein the inserter piece comprises one or more of a retention tool and a cutting tool.

23. The transforaminal lumbar interbody fusion method of claim 18, wherein the inserter piece is selectively articulatable with respect to the articulating joint mechanism.

24. An articulating transforaminal lumbar interbody fusion inserter device operable for placing, positioning, and inserting a spinal implant into an intervertebral space with minimum tissue disruption and maximum inline impaction forces, comprising:
an elongate shaft having a proximal end, a distal end, and an axis;
a handle disposed at the proximal end of the elongate shaft;
an articulating joint mechanism disposed at the distal end of the elongate shaft; and
an inserter piece coupled to the articulating joint mechanism, wherein the inserter piece is operable for selectively retaining the spinal implant, and
wherein the articulating joint mechanism is operable for selectively actuating the inserter piece between one or more substantially off-axis configurations and a substantially on-axis configuration with respect to the elongate shaft, and wherein the articulating joint mechanism comprises a base, a slotted capstan pivotably coupled to the base, and a locking bar configured to selectively engage/disengage the slotted capstan.

* * * * *